United States Patent
Tribble et al.

(10) Patent No.: US 12,180,260 B2
(45) Date of Patent: *Dec. 31, 2024

(54) T CELL RECEPTORS

(71) Applicant: Adaptimmune Limited, Abingdon (GB)

(72) Inventors: Nicholas Tribble, Abingdon (GB); William Lawrance, Abingdon (GB); Eleanor Bagg, Abingdon (GB)

(73) Assignee: Adaptimmune Limited, Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/339,663

(22) Filed: Jun. 22, 2023

(65) Prior Publication Data

US 2024/0218043 A1 Jul. 4, 2024

Related U.S. Application Data

(60) Continuation of application No. 17/501,122, filed on Oct. 14, 2021, now Pat. No. 11,725,040, which is a division of application No. 16/154,192, filed on Oct. 8, 2018, now Pat. No. 11,286,289, which is a continuation-in-part of application No. PCT/EP2017/058580, filed on Apr. 10, 2017.

(30) Foreign Application Priority Data

Apr. 8, 2016 (GB) ...................................... 1606177

(51) Int. Cl.
| | |
|---|---|
| *C07K 14/725* | (2006.01) |
| *A61K 35/17* | (2015.01) |
| *A61K 38/00* | (2006.01) |
| *A61K 38/17* | (2006.01) |
| *A61P 35/00* | (2006.01) |
| *C07K 14/47* | (2006.01) |
| *G01N 33/53* | (2006.01) |

(52) U.S. Cl.
CPC .......... *C07K 14/7051* (2013.01); *A61K 35/17* (2013.01); *A61P 35/00* (2018.01); *C07K 14/4748* (2013.01); *G01N 33/53* (2013.01); *A61K 38/00* (2013.01); *A61K 38/1774* (2013.01)

(58) Field of Classification Search
CPC . C07K 14/7051; C07K 14/4748; A61P 35/00; A61K 35/17; G01N 33/53
See application file for complete search history.

(56) References Cited

U.S. PATENT DOCUMENTS

| | | | |
|---|---|---|---|
| 7,388,072 B2 | 6/2008 | Zhang et al. | |
| 7,521,197 B2 | 4/2009 | Savage | |
| 7,666,604 B2 | 2/2010 | Jakobsen | |
| 10,117,918 B2 | 11/2018 | Sahin | |
| 11,286,289 B2 | 3/2022 | Tribble et al. | |
| 2004/0007704 A1 | 4/2004 | Zhang et al. | |
| 2009/0324566 A1 | 12/2009 | Shiku et al. | |
| 2012/0009162 A1* | 1/2012 | Yasukawa | A61K 31/7105 435/325 |
| 2014/0378389 A1 | 12/2014 | Robbins et al. | |
| 2019/0135892 A1 | 5/2019 | Tribble et al. | |
| 2019/0144521 A1 | 5/2019 | Tribble et al. | |
| 2022/0031753 A1 | 2/2022 | Tribble et al. | |

FOREIGN PATENT DOCUMENTS

| | | |
|---|---|---|
| CN | 101287831 A1 | 10/2008 |
| CN | 105163765 A | 12/2015 |
| CN | 106749620 A | 5/2017 |
| CN | 108366995 A | 8/2018 |
| CN | 110325633 A | 10/2019 |
| CN | 110582299 A | 12/2019 |
| CN | 110951690 A | 4/2020 |
| CN | 111315402 A | 6/2020 |
| CN | 113166778 A | 7/2021 |
| EP | 1930433 A1 | 6/2008 |
| JP | 2007527191 A | 9/2007 |
| JP | 2013541332 A | 11/2013 |
| KR | 102349677 | 1/2022 |
| KR | 102523449 | 4/2023 |
| RU | 2355703 C2 | 5/2009 |
| WO | 2000020445 A2 | 4/2000 |
| WO | 02094981 A2 | 11/2002 |

(Continued)

OTHER PUBLICATIONS

Ikeda et al. "In vivo persistence of adoptively transferred TCR gene-transduced lymphocytes with anti-tumor reactivity in patients with MAGE-A4 expressing esophageal cancer", J Immunother Cancer. 2013; 1(Suppl 1): O3 (Year: 2013).*
Aggen, et al., "Single-Chain V.alpha.V.beta. T Cell Receptors Function Without Mispairing With Endogenous TCR Chains", Gene Ther. Apr. 2012; 19(4): 365-374 (Year: 2012).
Anonymous: EMBL CDS: BAS03571: Sequence: UPI000676CA51 (Aug. 1, 2015) Retrieved from Internet: URL: http://www.uniprot.org/uniparc/UPI000676CA51. Retrieved on Sep. 6, 2017.
Anonymous: EMPB CDS: BAF94626—Sequence: UPI0001614056 (Dec. 30, 2007) Retrieved from Internet URL: http://www.uniprot.org/uniparc/UPI0001614056. Retrieved on Sep. 6, 2017.
Colman, "Effects of Amino Acid Sequence Changes on Antibody-Antigen Interactions", Biomolecular Research Institute, Research in Immunology, 1994, vol. 245, No. 1, pp. 33-36.

(Continued)

*Primary Examiner* — Amy E Juedes
*Assistant Examiner* — Peter Johansen
(74) *Attorney, Agent, or Firm* — Sheppard Mullin Richter & Hampton LLP

(57) ABSTRACT

The present invention relates to T cell receptors (TCRs) which bind the HLA-A*0201 restricted peptide GVYDGREHTV (SEQ ID NO: 1) derived from the MAGE-A4 protein. The TCRs of the invention demonstrate excellent specificity profiles for this MAGE epitope. Also provided are nucleic acids encoding the TCRs, cells engineered to present the TCRs, cells harbouring expression vectors encoding the TCRs and pharmaceutical compositions comprising the TCRs, nucleic acids or cells of the invention.

21 Claims, No Drawings

Specification includes a Sequence Listing.

(56) References Cited

FOREIGN PATENT DOCUMENTS

| WO | 2004074322 A1 | 9/2004 |
|---|---|---|
| WO | 2012038055 A1 | 3/2012 |
| WO | WO 2012054825 A1 | 4/2012 |
| WO | WO 2013039889 A1 | 3/2013 |
| WO | WO 2016055785 A1 | 10/2015 |
| WO | WO 2016191756 A1 | 12/2016 |
| WO | WO 2018055140 A1 | 3/2018 |
| WO | WO 2018170338 | 3/2018 |

OTHER PUBLICATIONS

Cordoba, et al., "The Large Ectodomains of CD45 and CD148 Regulate Their Segregation from the Inhibition of Ligated T-Cell Receptor", Blood, May 23, 2013, vol. 121, No. 21, pp. 4295-4302.

De la Hera, et al., "Structure of the T Cell Antigen Receptor (TCR) Two CD3e Subunits in a Functional TCR/CD3 Complex", J. Exp. Med., vol. 173, Jan. 1991, pp. 7-17.

Duffour, et al., "A MAGE-A4 Peptide Presented by HLA-A2 is Recognized by Cytolytic T Lymphocytes", Eur. J. Immunol . . . 1999, vol. 29, pp. 3329-3337.

English translation of Chinese Office Action issued Jun. 1, 2021, in corresponding Chinese Appln. No. 2017800317102.

Gasser, et al., "Antibody Production with Yeast and Filamentous Fungi: On the Road to Large Scale?", Biotechnol. Lett (2007) vol. 29, No. 2, p. 201-212.

Hillig, et al., "High-resolution Structure of HLA-A*0201 in Complex with a Tumour-specific Antigenic Peptide Encoded by the MAGE-A4 Gene", J. Mol. Biol. (2001) vol. 310, p. 1167-1176.

Holler, et al., "Quantitative Analysis of the Contribution of TCR/pepMHC Affinity and CD8 to T Cell Activation", Immunity (Feb. 2003) vol. 18, p. 255-264.

International Search Report dated Sep. 18, 2017 in International Application No. PCT/EP2017/058580.

Ma, et al., "Identification of Two Novel HLA-A*0201-Restricted CTL Epitopes Derived from MAGE-A4", Clinical and Developmental Immunology, vol. 2010, Artilce 567594, 7 pages, 2010.

Office Action dated Aug. 8, 2021, in counterpart Korean Application No. 10-2018-7032168.

Office Action dated May 21, 2021 in corresponding Japanese Application No. 2018-552872.

Ozawa, et al., "Comprehensive analysis of the functional TCR repertoireat the single-cell level", Biochemical and Biophysical Research Communications 367 (2008) 820-825.

Pakula, et al., "Genetic Analysis of Protein Stability and Function", Annu. Rev. Genet. (1989) vol. 23, p. 289-310.

Rudikoff, et al., "Single amino acid substitution altering antigen-binding specificity", Proc Natl Acad Sci U S A. Mar. 1982; 79(6): 1979-1983. (Year:1982).

Russian Search Report dated Jul. 30, 2020.

Safdari, et al., "Antibody Humanization Methods—A Review and Update", Biotechnology and Genetic Engineering Reviews, vol. 29, No. 2, pp. 175-186, 2013.

Wahl, et al., "HLA Class I Molecules Reflect an Altered Host Proteome After Influenza Virus Infection", Human Immunology (2010) vol. 71, p. 14-22.

Fidler, "Biololgical heterogeneity of cancer," Human Vaccine Immunotherapeutics, Aug. 2012, vol. 8, Issue 8, pp. 1141-1142.

Fujiwara-Kuroda et al., "Prognostic value of MAGEA4 in primary lung cancer depends on subcellular localization and p53 status," International Journal of Oncology, 2018, vol. 53, Issue 2, pp. 713-724.

Gale, "Cellular and Molecular Basis of Cancer," Merck Manuals Professional Edition, 2020, <URL: https://www.merckmanuals.com/professional/hematology-and-oncology/overview-of-cancer/cellular-and-molecular-basis-of-cancer>.

Ikeda et al., "In vivo persistence of adoptively transferred TCR gene-transduced lymphocytes with anti-tumor reactivity in patients with MAGE-A4 expressing esophageal cancer", J Immunother Cancer. 2013; 1 (Suppl 1 ): 03. (Year: 2013).

The Merck Manuals Online Medical Library, [online]. Whitehouse Station, NJ: Merck Research Laboratories, 2006-2007. [retrieved on Oct. 19, 2020]. < URL: https://www.merckmanuals.com/professional/hematology-and-oncology/overview-of-cancer/ cellular-and-molecular-basis-of-cancer> (Year: 2020).

Bajwa et all "440. Reprogramming CD4 T Cells into Cytotoxic CD8 Cells by Forced Expression of CD8αβ and Class I Restricted T Cell Receptors", Molecular Therapy, May 2018,vol. 26, No. 5S1,p. 20.

Bethune Michael T., et al., "Isolation and characterization of NY-ESO-1-specific T cell receptors restricted on various MHC molecules11", Proceedings of the National Academy of Sciences of the United States of America, vol. 115, No. 15, pp. E10702-E10711, Nov. 6, 2018.

Chinese Office Action dated Jul. 10, 2024 for Chinese Patent Application No. 201980089522.4, 20 pages with English translation.

Chua I.C., CD8 co-receptor modifications to enhance T cell immunotherapy, 2013, Thesis, pp. 1-193.

Dorrie et al.: "Human Adenovirus specific γ/δ and CD8+ cells generated by T-Cell receptor transfection to treat adenovirus infection after allogeneic stem cell transplantation" PLoS ONE,2014,vol. 9, No. 10,e109944 (pp. 1-10),doi:10.1371/journal.pone.0109944.

Hiasa et al "Long-term phenotypic, functional and genetic stability of cancer-specific T-cell receptor (TCR) a genes transduced to cos+ T cells" Gene Therapy 2008, vol. 15, pp. 695-699.

International Search Report in International Patent Application No. PCT/EP2019/083196 mailed Feb. 26, 2021.

Japanese Office Action dated Oct. 10, 2023 for Japanese Patent Application No. 2021-530124, 12 pages with English translation.

Japanese Office Action dated Mar. 12, 2024, for Japanese Patent Application No. 2021-530124, 13 pages with English translation.

Lyons et al "Influence of Human CDS on Antigen Recognition by T-Cell Receptor-Transduced Cells" Cancer Res, 2006, vol. 66, No. 23, pp. 11455-11461, doi: 10.1158/0008-5472.CAN-06-2379.

Soto, Carolina M., et al., "MHC-class I-restricted CD4 T cells: a nanomolar affinity TCR has improved anti-tumor fficacy in vivo compared to the micromolar wild-type TCR11", Cancer Immunology Immunotherapy, vol. 62, No. 2, pp. 359-369, Feb. 2013.

Zhou et al: "T-cell receptor gene transfer exclusively to human CD8+ cells enhances tumor cell killing" Blood,2012,vol. 120, No. 22,pp. 4334-4342,DOI.

* cited by examiner

T CELL RECEPTORS

CROSS-REFERENCE TO RELATED APPLICATIONS

This application is a continuation of U.S. application Ser. No. 17/501,122, filed Oct. 14, 2021, which is a division of U.S. application Ser. No. 16/154,192, filed Oct. 8, 2018, now U.S. Pat. No. 11,286,289, which is a continuation-in-part application of International Patent Application No. PCT/EP2017/058580, filed Apr. 10, 2017, which claims the benefit of GB Application No. 1606177.2, filed Apr. 8, 2016, the content of each of which is incorporated herein by reference in its entirety.

REFERENCE TO AN ELECTRONIC SEQUENCE LISTING

The contents of the electronic sequence listing (PC10016.xml; Size: 39,134 bytes; and Date of Creation: Aug. 17, 2022) is herein incorporated by reference in its entirety.

FIELD OF THE INVENTION

The present invention relates to T cell receptors (TCRs) which bind the HLA-A*0201 restricted decapeptide GVYDGREHTV (SEQ ID NO: 1) derived from the melanoma-associated antigen (MAGE) A4 protein (amino acids 230-239). The TCRs of the invention demonstrate excellent specificity profiles for this MAGE epitope.

BACKGROUND TO THE INVENTION

Cancer testis antigens (CTA) are a subclass of tumor-associated antigen (TAA) encoded by approximately 140 genes. Expression of these antigens is restricted in immune privileged sites such as the testes, placenta and fetal ovary; they are typically not expressed in other tissues.

Expression of these genes has been observed in malignant tumors. The immunogenicity of CTA has led to the widespread development of cancer vaccines targeting these antigens in many solid tumors. Within this large class of TAA, melanoma-associated antigens (MAGE) have emerged as promising candidates for cancer immunotherapy.

More than 30 cancer testis (CT) genes have been reported as members of multi-gene families that are organized into gene clusters on chromosome X (CT-X antigens). The CT gene clusters are located between Xq24 and Xq28 and include gene families such as MAGE and NY-ESO-1. Type I MAGE gene clusters are the most extensively characterized and include the MAGE-A, MAGE-B and MAGE-C families. The MAGE-A proteins are encoded by 12 different MAGE-A gene family members (MAGE-A1 to MAGE-A12) and are defined by a conserved 165-171 amino acid base, called the MAGE homology domain (MHD). The MHD corresponds to the only region of shared amino acids by all of the MAGE-A family members.

T cells recognize and interact with complexes of cell surface molecules, referred to as human leukocyte antigens ("HLA"), or major histocompatibility complexes ("MHCs"), and peptides. The peptides are derived from larger molecules, which are processed by the cells which also present the HLA/MHC molecule. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. The mechanism is involved in the immune system's response to infection, in autoimmune disease, and in responses to abnormalities such as tumors.

Some MAGE gene family proteins are only expressed in germ cells and cancer (MAGE-A to MAGE-C families). Others are widely expressed in normal tissues (MAGE-D through to MAGE-H). All these MAGE protein families have a homologous region that is closely matched to the sequence of the other MAGE proteins and comprises peptides displayed as HLA/peptide complexes in immune recognition. Hence, it is important to select TCR clinical candidates that are highly specific for the desired MAGE peptide/HLA-A2 antigen.

MAGE A4 is a CTA member of the MAGE A gene family. The function is unknown, though it is thought that it may play a role in embryonal development. In tumor pathogenesis, it appears to be involved in tumor transformation or aspects of tumor progression. MAGE A4 has been implicated in a large number of tumors, including seminoma, dyskeratosis congenital, melanoma, hepatocellular carcinoma, renal cell carcinoma, pancreatic cancer, lung cancer, colorectal cancer and breast cancer. The peptide GVYDGREHTV (SEQ ID NO: 1) corresponds to amino acid residue numbers 230-239 of the known MAGE-A4 protein.

MAGE B2 is a CTA of the MAGE B gene family. MAGE B2 is expressed in testis and placenta, and in a significant fraction of tumors of various histological types. The peptide GVYDGEEHSV (SEQ ID NO: 2) shows cross-reactivity with MAGE A4, such that certain TCRs are able to bind to HLA molecules displaying both peptides.

SUMMARY OF THE INVENTION

We have developed a TCR which binds to HLA molecules displaying the MAGE A4 peptide GVYDGREHTV (SEQ ID NO: 1) in preference to MAGE B2. In a first aspect, the present invention provides a T cell receptor (TCR) having the property of binding to GVYDGREHTV (SEQ ID NO: 1) in complex with HLA-A*0201 with a dissociation constant of from about 0.05 µM to about 20.0 µM when measured with surface plasmon resonance at 25° C. and at a pH between 7.1 and 7.5 using a soluble form of the TCR, wherein the TCR comprises a TCR alpha chain variable domain and a TCR beta chain variable domain, and wherein the TCR variable domains form contacts with at least residues V2, Y3 and D4 of GVYDGREHTV (SEQ ID NO: 1).

In embodiments, the TCR according to the invention has the property of binding to GVYDGEEHSV (SEQ ID NO: 2) in complex with HLA-A*0201 with a dissociation constant of from about 20 µM to about 50 µM when measured with surface plasmon resonance at 25° C. and at a pH between 7.1 and 7.5 using a soluble form of the TCR, wherein the TCR comprises a TCR alpha chain variable domain and a TCR beta chain variable domain. In some embodiments, the dissociation constant is above 50 microM, such as 100 µM, 200 µM, 500 µM or more.

Accordingly, a TCR in accordance with the invention is capable of binding efficiently to HLA displaying GVYDGREHTV (SEQ ID NO: 1) but not to HLA displaying GVYDGEEHSV (SEQ ID NO: 2).

In some embodiments, the alpha chain variable domain of the TCR comprises an amino acid sequence that has at least 80% identity to the sequence of amino acid residues 1-105 of SEQ ID NO: 3 (alpha chain), and/or the beta chain variable domain comprises an amino acid sequence that has at least 80% identity to the sequence of amino acid residues 1-123 of SEQ ID NO: 4 (beta chain).

In a further aspect, the present invention provides a T cell receptor (TCR) having the property of binding to GVYDGREHTV (SEQ ID NO: 1) in complex with HLA-A*0201 and comprising a TCR alpha chain variable domain and a TCR beta chain variable domain, the alpha chain variable domain comprising an amino acid sequence that has at least 80% identity to the sequence of amino acid residues 1-105 of SEQ ID NO: 3, and/or the beta chain variable domain comprising an amino acid sequence that has at least 80% identity to the sequence of amino acid residues 1-123 of SEQ ID NO: 4.

The GVYDGREHTV (SEQ ID NO: 1) HLA-A2 complex provides a cancer marker that the TCRs of the invention can target. The present invention provides such TCRs useful for the purpose of delivering cytotoxic or immune effector agents to the cancer cells and/or useful for use in adoptive therapy.

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The α and β chains of αβ TCR's are generally regarded as each having two "domains", namely variable and constant domains. The variable domain consists of a concatenation of variable region and joining region. In the present specification and claims, the term "TCR alpha variable domain" therefore refers to the concatenation of TRAV and TRAJ regions, and the term TCR alpha constant domain refers to the extracellular TRAC region, or to a C-terminal truncated TRAC sequence. Likewise the term "TCR beta variable domain" refers to the concatenation of TRBV and TRBD/TRBJ regions, and the term TCR beta constant domain refers to the extracellular TRBC region, or to a C-terminal truncated TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

One TCR in accordance with the invention comprises an alpha chain extracellular domain as shown in SEQ ID NO: 3 (TRAV10+TRAC) and a beta chain extracellular domain as shown in SEQ ID NO: 4 (TRBV24-1+TRBC-2). The terms "parental TCR", "parental MAGE-A4 TCR", are used synonymously herein to refer to this TCR comprising the extracellular alpha and beta chain of SEQ ID Nos: 2 and 3 respectively. It is desirable to provide TCRs that are mutated or modified relative to the parental TCR that have a higher affinity and/or a slower off-rate for the peptide-HLA complex than the parental TCR.

For the purpose of providing a reference TCR against which the binding profile of such mutated or modified TCRs may be compared, it is convenient to use a soluble TCR in accordance with the invention having the extracellular sequence of the parental MAGE-A4 TCR alpha chain given in SEQ ID NO: 3 and the extracellular sequence of the parental MAGE-A4 TCR beta chain given in SEQ ID NO: 4. That TCR is referred to herein as the "the reference TCR" or "the reference MAGE-A4 TCR". Note that SEQ ID NO: 5 comprises the parental alpha chain extracellular sequence of SEQ ID NO: 3 and that C162 has been substituted for T162 (i.e. T48 of TRAC). Likewise SEQ ID NO: 6 is the parental beta chain extracellular sequence of SEQ ID NO: 4 and that C169 has been substituted for S169 (i.e. S57 of TRBC2), A187 has been substituted for C187 and D201 has been substituted for N201. These cysteine substitutions relative to the parental alpha and beta chain extracellular sequences enable the formation of an interchain disulfide bond which stabilises the refolded soluble TCR, i.e. the TCR formed by refolding extracellular alpha and beta chains. Use of the stable disulfide linked soluble TCR as the reference TCR enables more convenient assessment of binding affinity and binding half life. TCRs of the invention may comprise the mutations described above.

TCRs of the invention may be non-naturally occurring and/or purified and/or engineered. TCRs of the invention may have more than one mutation present in the alpha chain variable domain and/or the beta chain variable domain relative to the parental TCR. "Engineered TCR" and "mutant TCR" are used synonymously herein and generally mean a TCR which has one or more mutations introduced relative to the parental TCR, in particular in the alpha chain variable domain and/or the beta chain variable domain thereof. These mutation(s) may improve the binding affinity for GVYDGREHTV (SEQ ID NO: 1) in complex with HLA-A*020101. In certain embodiments, there are 1, 2, 3, 4, 5, 6, 7 or 8 mutations in alpha chain variable domain, for example 4 or 8 mutations, and/or 1, 2, 3, 4 or 5 mutations in the beta chain variable domain, for example 5 mutations. In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-105 of SEQ ID NO: 3. In some embodiments, the β chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-123 of SEQ ID NO: 4.

The alpha chain variable domain of a TCR of the invention may have the following mutation:

| M51 | V or L |
|---|---| with reference to the numbering shown in SEQ ID NO: 3, and/or
the beta chain variable domain may have at least one of the following mutations:

| N119 | E |
|---|---| with reference to the numbering shown in SEQ ID NO: 4.

The alpha chain variable domain of a TCR of the invention may comprise the amino acid sequence of amino acid residues 1-105 of SEQ ID NO:3, 5 or 7 to 8
or an amino acid sequence in which amino acid residues 1-27, 34-47, and 54-90 thereof have at least 90% or 95% identity to the sequence of amino acid residues 1-27, 34-47, and 54-90 respectively of SEQ ID NO: 3, 5 or 7 to 8 and in which amino acid residues 28-33, 48-53 and 91-105 have at least 90% or 95% identity to the sequence of amino acid residues 28-33, 48-53 and 91-105 respectively of SEQ ID NO: 3, 5 or 7 to 8.

In the alpha chain variable domain, the sequence of
(i) amino acid residues 1-27 thereof may have (a) at least 90% identity to the sequence of amino acid residues 1-27 of SEQ ID NO: 3 or (b) may have one, two or three amino acid residues inserted or deleted relative to the sequence of (a);
(ii) amino acid residues 28-33 of SEQ ID NO: 3;
(iii) amino acid residues 34-47 thereof may have (a) at least 90% identity to the sequence of amino acid residues 34-47 of SEQ ID NO: 3 or (b) may have one, two or three amino acid residues inserted or deleted relative to the sequence of (a);
(iv) amino acid residues 48-53 may be of SEQ ID NO: 3 or amino acid residues 48-50, 52 and 53 of SEQ ID NO: 3 with amino acid residue 51 of SEQ ID NO: 3 substituted with β instead of I or amino acid residues 48-50, 52 and 53 of SEQ ID NO: 3 with amino acid residue 51 of SEQ ID NO: 3 substituted with V instead of I or amino acid residues 48-51 and 53 of SEQ ID NO: 3 with amino acid residue 52 of SEQ ID NO: 3 substituted with L instead of M;
(v) amino acid residues 54-90 thereof may have at least 90% identity to the sequence of amino acid residues 54-90 of SEQ ID NO: 3 or may have one, two or three insertions, deletions or substitutions relative thereto;
(vi) amino acids 91-105 of SEQ ID NO: 3.

The beta chain variable domain of a TCR of the invention may comprise the amino acid sequence of SEQ ID NO: 4 or 6 or 9
or an amino acid sequence in which amino acid residues 1-45, 51-67, 73-109 thereof have at least 90% or 95% identity to the sequence of amino acid residues 1-45, 51-67, 73-109 respectively of SEQ ID NO: 4 or 9 and in which amino acid residues 46-50, 68-72 and 110-123 have at least 90% or 95% identity to the sequence of amino acid residues 46-50, 68-72 and 110-123 respectively of SEQ ID NO: 4 or 9.

In the beta chain variable domain, the sequence of
(i) amino acid residues 1-45 thereof may have (a) at least 90% identity to the amino acid sequence of residues 1-45 of SEQ ID NO: 4 or (b) may have one, two or three amino acid residues inserted or deleted relative to the sequence of (a);
(ii) amino acid residues 46-50 of SEQ ID NO: 4;
(iii) amino acid residues 51-67 thereof may have (a) at least 90% identity to the sequence of amino acid residues 51-67 of SEQ ID NO: 4 or (b) may have one, two or three amino acid residues inserted or deleted relative to the sequence of (a);
(iv) amino acid residues 68-72 of SEQ ID NO: 4;
(v) amino acid residues 73-109 thereof may have (a) at least 90% identity to the sequence of amino acid residues 73-109 of SEQ ID NO: 4 or (b) may have one, two or three amino acid residues inserted or deleted relative to the sequence of (a);
(vi) amino acid residues 110-123 of SEQ ID NO: 4 or amino acid residues 110-118 and 120-123 of SEQ ID NO: 4 with amino acid residue 119 of SEQ ID NO: 4 substituted with β instead of N.

A TCR of the invention may have one of the following combinations of alpha and beta chain variable domains:

| Alpha Chain SEQ ID NO: | Beta Chain SEQ ID NO: |
|---|---|
| 3 | 4 |
| 3 | 6 |
| 3 | 9 |
| 5 | 4 |
| 5 | 6 |
| 5 | 9 |
| 7 | 4 |
| 7 | 6 |
| 7 | 9 |
| 8 | 4 |
| 8 | 6 |
| 8 | 9 |

Within the scope of the invention are phenotypically silent variants of any TCR of the invention disclosed herein. As used herein the term "phenotypically silent variants" is understood to refer to a TCR which incorporates one or more further amino acid changes in addition to those set out above which TCR has a similar phenotype to the corresponding TCR without said change(s). For the purposes of this application, TCR phenotype comprises antigen binding specificity ($K_D$ and/or binding half life) and antigen specificity. A phenotypically silent variant may have a $K_D$ and/or binding half-life for the GVYDGREHTV (SEQ ID NO: 1) HLA-A*0201 complex within 10% of the measured $K_D$ and/or binding half-life of the corresponding TCR without said change(s), when measured under identical conditions (for example at 25° C. and on the same SPR chip). Suitable conditions are further defined in Example 3. Antigen specificity is further defined below. As is known to those skilled in the art, it may be possible to produce TCRs that incorporate changes in the constant and/or variable domains thereof compared to those detailed above without altering the affinity for the interaction with the GVYDGREHTV (SEQ ID NO: 1) HLA-A*0201 complex. In particular, such silent mutations may be incorporated within parts of the sequence that are known not to be directly involved in antigen binding (e.g. outside the CDRs). Such trivial variants are included in the scope of this invention. Those TCRs in which one or more conservative substitutions have been made also form part of this invention.

Mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual ($3^{rd}$ Ed.) CSHL Press. Further information on ligation independent cloning (LIC) procedures can be found in Rashtchian, (1995) *Curr Opin Biotechnol* 6(1): 30-6.

The TCRs of the invention have the property of binding the MAGE-A4 peptide, GVYDGREHTV (SEQ ID NO: 1) HLA-A2 complex. The TCRs of the invention have been found to be highly specific for those MAGE epitopes relative to other, irrelevant epitopes, and are thus particularly suitable as targeting vectors for delivery of therapeutic agents or detectable labels to cells and tissues displaying those epitopes. Specificity in the context of TCRs of the invention relates to their ability to recognise HLA-A*0201 target cells that are positive for the peptide GVYDGREHTV (SEQ ID NO: 1), whilst having minimal ability to recognise HLA-A*0201 target cells that are negative for the peptide, or HLA cells that display the MAGE B2 peptide GVYDGEEHSV (SEQ ID NO: 2). To test specificity, the TCRs may be in soluble form and/or may be expressed on the surface of T cells. Recognition may be determined by measuring the level of T cell activation in the presence of a TCR and target cells. In this case, minimal recognition of peptide negative or MAGE B2 target cells is defined as a level of T cell activation of less than 10%, preferably less than 5%, and more preferably less than 1%, of the level produced in the presence of peptide positive target cells, when measured under the same conditions. For soluble TCRs of the invention, specificity may be determined at a therapeutically relevant TCR concentration. A therapeutically relevant concentration may be defined as a TCR concentration of $10^{-9}$ M or below, and/or a concentration of up to 100, preferably up to 1000, fold greater than the corresponding EC50 value. Peptide positive cells may be obtained by peptide-pulsing or, more preferably, they may naturally present said peptide. Preferably, both peptide positive and peptide negative cells are human cells.

Certain TCRs of the invention have been found to be highly suitable for use in adoptive therapy. Such TCRs may have a $K_D$ for the complex of less than the 200 µM, for example from about 0.05 µM to about 20 µM or about 100 µM and/or have a binding half-life (T½) for the complex in the range of from about 0.5 seconds to about 12 minutes. In some embodiments, TCRs of the invention may have a $K_D$ for the complex of from about 0.05 µM to about 20 µM, about 0.1 µM to about 5 µM or about 0.1 µM to about 2 µM. Without wishing to be bound by theory, there seems to be an optimum window of affinity for TCRs with therapeutic use in adoptive cell therapy. Naturally occurring TCRs recognising epitopes from tumour antigens are generally of too low affinity (20 microM to 50 microM) and very high affinity TCRs (in the nanomolar range or higher) suffer from cross-reactivity issues (Robbins et al (2008) J. Immunol. 180 6116-6131; Zhao et al (2007) J. Immunol. 179 5845-5854; Scmid et al (2010) J. Immunol 184 4936-4946).

The TCRs of the invention may be αβ heterodimers or may be in single chain format. Single chain formats include αβ TCR polypeptides of the Vα-L-Vβ, Vβ-L-Vα, Vα-Cα-L-Vβ or Vα-L-Vβ-Cβ types, wherein Vα and Vβ are TCR α and β variable regions respectively, Cα and Cβ are TCR α and β constant regions respectively, and L is a linker sequence. For use as a targeting agent for delivering therapeutic agents to the antigen presenting cell the TCR may be in soluble form (i.e. having no transmembrane or cytoplasmic domains). For stability, soluble αβ heterodimeric TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full length chains having both cytoplasmic and transmembrane domains. TCRs for use in adoptive therapy may contain a disulphide bond corresponding to that found in nature between the respective alpha and beta constant domains, additionally or alternatively a non-native disulphide bond may be present.

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present invention.

Alpha-beta heterodimeric TCRs of the invention usually comprise an alpha chain TRAC constant domain sequence and a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and beta chain constant domain sequences may also be modified by substitution of cysteine residues for Thr 48 of TRAC and Ser 57 of TRBC1 or TRBC2, the said cysteines forming a disulfide bond between the alpha and beta constant domains of the TCR.

Some TCRs of the invention have a binding affinity for, and/or a binding half-life for, the GVYDGREHTV (SEQ ID NO: 1)-HLA-A2 complex substantially higher than that of the reference MAGE-A4 TCR, Increasing the binding affinity of a native TCR often reduces the specificity of the TCR for its peptide-MHC ligand, and this is demonstrated in Zhao Yangbing et al., The Journal of Immunology, The American Association of Immunologists, US, vol. 179, No. 9, 1 Nov. 2007, 5845-5854. However, the TCRs of the invention which are derived from the parental TCR remain specific for the GVYDGREHTV (SEQ ID NO: 1)-HLA-A2 complex, despite having substantially higher binding affinity than the parental TCR. Moreover, they are significantly more (e.g. at least ten-fold) selective for MAGE-A4 over MAGE-B2 than the parental TCR.

Binding affinity (inversely proportional to the equilibrium constant $K_D$) and binding half-life (expressed as T½) can be determined using the Surface Plasmon Resonance (BIAcore) method of Example 3 herein. Measurements may be carried out at 25° C. and at a pH between 7.1 and 7.5 using a soluble version of the TCR. It will be appreciated that doubling the affinity of a TCR results in halving the $K_D$. T½ is calculated as ln 2 divided by the off-rate ($k_{off}$). So doubling of T½ results in a halving in $k_{off}$. $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for, the GVYDGREHTV (SEQ ID NO: 1)-HLA-A2 complex if a soluble form of that TCR meets that requirement. Preferably the binding affinity or binding half-life of a given TCR is measured several times, for example 3 or more times, using the same assay protocol, and an average of the results is taken. The reference MAGE-A4 TCR has a $K_D$ of approximately 65 μM as measured by that method, and its $k_{off}$ is approximately) 0.73 s$^{-1}$ (i.e T½ is approximately 0.95 s).

In a further aspect, the present invention provides nucleic acid encoding a TCR of the invention. In some embodiments, the nucleic acid is cDNA. In some embodiments, the invention provides nucleic acid comprising a sequence encoding an α chain variable domain of a TCR of the invention. In some embodiments, the invention provides nucleic acid comprising a sequence encoding a β chain variable domain of a TCR of the invention. The nucleic acid may be non-naturally occurring and/or purified and/or engineered.

In another aspect, the invention provides a vector which comprises nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which comprises nucleic acid encoding the alpha chain of a TCR of the invention, and a second expression vector which comprises nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) *J Immunol.* 180: 6116-6131). T cells expressing the TCRs of the invention will be suitable for use in adoptive therapy-based treatment of cancer. As will be known to those skilled in the art, there are a number of suitable methods by which adoptive therapy can be carried out (see for example Rosenberg et al., (2008) *Nat Rev Cancer* 8(4): 299-308).

Soluble TCRs of the invention are useful for delivering detectable labels or therapeutic agents to the antigen presenting cells and tissues containing the antigen presenting cells. The may therefore be associated (covalently or otherwise) with a detectable label (for diagnostic purposes wherein the TCR is used to detect the presence of cells presenting the GVYDGREHTV (SEQ ID NO: 1)-HLA-A2 complex); a therapeutic agent; or a PK modifying moiety (for example by PEGylation).

Detectable labels for diagnostic purposes include for instance, fluorescent labels, radiolabels, enzymes, nucleic acid probes and contrast reagents.

Therapeutic agents which may be associated with the TCRs of the invention include immunomodulators, radioactive compounds, enzymes (perforin for example) or chemotherapeutic agents (cisplatin for example). To ensure that toxic effects are exercised in the desired location the toxin could be inside a liposome linked to TCR so that the compound is released slowly. This will prevent damaging effects during the transport in the body and ensure that the toxin has maximum effect after binding of the TCR to the relevant antigen presenting cells.

Other suitable therapeutic agents include:
small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;

peptide cytotoxins, i.e. proteins or fragments thereof with the ability to kill mammalian cells. For example, ricin, diphtheria toxin, pseudomonas bacterial exotoxin A, DNase and RNase;

radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

immuno-stimulants, i.e. immune effector molecules which stimulate immune response. For example, cytokines such as IL-2 and IFN-γ, Superantigens and mutants thereof;

TCR-HLA fusions;

chemokines such as IL-8, platelet factor 4, melanoma growth stimulatory protein, etc;

antibodies or fragments thereof, including anti-T cell or NK cell determinant antibodies (e.g. anti-CD3, anti-CD28 or anti-CD16);

alternative protein scaffolds with antibody like binding characteristics complement activators;

xenogeneic protein domains, allogeneic protein domains, viral/bacterial protein domains, viral/bacterial peptides.

One preferred embodiment is provided by a TCR of the invention associated (usually by fusion to an N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab')$_2$ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (Pieris (German), comprising engineered anticalins) to name but a few.

For some purposes, the TCRs of the invention may be aggregated into a complex comprising several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment. (Willuda et al. (2001) J. Biol. Chem. 276 (17) 14385-14392). Haemoglobin also has a tetramerisation domain that could potentially be used for this kind of application. A multivalent TCR complex of the invention may have enhanced binding capability for the GVYDGREHTV (SEQ ID NO: 1) HLA-A2 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody-based therapeutics. (Jefferis R., Nat Rev Drug Discov. 2009 March; 8(3):226-34.). For soluble TCRs of the invention glycosylation may be controlled in vivo, by using particular cell lines for example, or in vitro, by chemical modification. Such modifications are desirable, since glycosylation can improve phamacokinetics, reduce immunogenicity and more closely mimic a native human protein (Sinclair A M and Elliott S., Pharm Sci. 2005 August; 94(8):1626-35).

For administration to patients, the TCRs, nucleic acids and/or cells of the invention (usually associated with a detectable label or therapeutic agent), may be provided in a pharmaceutical composition together with a pharmaceutically acceptable carrier or excipient. Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

TCRs, pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
- A TCR, nucleic acid or cell of the invention for use in medicine, preferably for use in a method of treating cancer, such as solid tumours (e.g., lung, liver and gastric metastases) and/or squamous cell carcinomas.
- the use of a TCR, nucleic acid or cell of the invention in the manufacture of a medicament for treating cancer.
- a method of treating cancer in a patient, comprising administering to the patient a TCR, nucleic acid or cell of the invention.

Preferred features of each aspect of the invention are as for each of the other aspects mutatis mutandis. The prior art documents mentioned herein are incorporated to the fullest extent permitted by law.

The invention is further described in the following non-limiting examples.

Reference is made to the enclosed sequences, in which:
- SEQ ID NO: 1 is the MAGE A4 peptide
- SEQ ID NO: 2 is the MAGE B2 peptide
- SEQ ID NO: 3 is the amino acid sequence of the extracellular part of the alpha chain of a parental MAGE-A4-specific TCR, and SEQ ID NO: 4 shows the amino acid sequence of the extracellular part of the beta chain of a parental MAGE-A4-specific TCR beta chain amino acid sequence.
- SEQ ID NO: 5 shows the amino acid sequence of the alpha chain of a native Lenti TCR (referred to herein as the "reference TCR"). The sequence is the same as that of The parental TCR except that a cysteine is substituted for T162 (i.e. T48 of the TRAC constant region).
- SEQ ID NO: 6 is the beta chain of a native Lenti TCR (referred to herein as the "reference TCR). The sequence is the same as that of the parental TCR except that a cysteine is substituted for S169 (i.e. S57 of the TRBC2 constant region) and A187 is substituted for C187 and D201 is substituted for N201.
- SEQ ID NOs: 7 and 8 show the sequences of alpha chains which may be present in TCRs of the invention. The subsequences forming the CDR regions, or substantial parts of the CDR regions, are underlined.
- SEQ ID NO: 9 shows the sequence of the beta chain which may be present in TCRs of the invention. The subsequences forming the CDR regions, or substantial parts of the CDR regions are underlined.
- SED ID NOs: 10 to 15 show the sequences of soluble alpha and beta chains of TCRs A, B and C. None of these TCRs could be developed into a functional TCR in accordance with the present invention.

EXAMPLES

Example 1—Cloning of the Reference MAGE-A4 TCR Alpha And Beta Chain Variable Region Sequences into pGMT7-Based Expression Plasmids The parental MAGE-A4 TCR variable alpha and TCR variable beta domains of SEQ ID NOS: 3 and 4 respectively were cloned into pGMT7-based expression plasmids containing either Cα or Cβ by standard methods described in (Molecular Cloning a Laboratory Manual Third edition by Sambrook and Russell). Plasmids were sequenced using an Applied Biosystems 3730×1 DNA Analyzer. The reference MAGE-A4 TCR variable alpha and TCR variable beta domains of SEQ ID NOS: 4 and 5 respectively were cloned in the same way.

The DNA sequence encoding the TCR alpha chain variable region was ligated into pEX956, which was cut with restriction enzymes. The DNA sequence encoding the TCR beta chain variable region was ligated into pEXb21, which was also cut with restriction enzymes.

Ligated plasmids were transformed into competent E. coli strain XL1-blue cells and plated out on LB/agar plates containing 100 μg/mL ampicillin. Following incubation overnight at 37° C., single colonies were picked and grown in 5 mL LB containing 100 μg/mL ampicillin overnight at 37° C. with shaking. Cloned plasmids were purified using a Miniprep kit (Qiagen) and the plasmids were sequenced using an Applied Biosystems 3730xl DNA Analyzer.

Example 2—Expression, Refolding and Purification of Soluble Reference MAGE-A4 TCR The expression plasmids containing the reference TCR α-chain and β-chain respectively, as prepared in Example 1, were transformed separately into E. coli strain BL21pLysS, and single ampicillin-resistant colonies were grown at 37° C. in TYP (ampicillin 100 μg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 15 mg of TCR α chain and 15 mg of TCR β chain solubilised inclusion bodies were thawed from frozen stocks and diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectrapor 1 membrane (Spectrum; Product No. 132670) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS 50HQ anion exchange column and eluting bound protein with a gradient of 0-500 mM NaCl in 10 mM Tris pH 8.1 over 50 column volumes using an Akta purifier (GE Healthcare). Peak fractions were pooled and a cocktail of protease inhibitors (Calbiochem) were added. The pooled fractions were then stored at 4° C. and analysed by Coomassie-stained SDS-PAGE before being pooled and concentrated. Finally, the soluble TCR was purified and characterised using a GE Healthcare Superdex 75HR gel filtration column pre-equilibrated in PBS buffer (Sigma). The peak eluting at a relative molecular weight of approximately 50 kDa was pooled and concentrated prior to characterization by BIAcore surface plasmon resonance analysis.

Example 3—Binding Characterisation

BIAcore Analysis

A surface plasmon resonance biosensor (BIAcore 3000™) can be used to analyse the binding of a soluble TCR to its peptide-MHC ligand. This is facilitated by producing soluble biotinylated peptide-HLA ("pHLA") complexes which can be immobilized to a streptavidin-coated binding surface (sensor chip). The sensor chips comprise four individual flow cells which enable simultaneous measurement of T-cell receptor binding to four different pHLA complexes. Manual injection of pHLA complex allows the precise level of immobilised class I molecules to be manipulated easily.

Biotinylated class I HLA-A*0201 molecules were refolded in vitro from bacterially-expressed inclusion bodies containing the constituent subunit proteins and synthetic peptide, followed by purification and in vitro enzymatic biotinylation (O'Callaghan et al. (1999) Anal. Biochem. 266: 9-15). HLA-A*0201-heavy chain was expressed with a C-terminal biotinylation tag which replaces the transmembrane and cytoplasmic domains of the protein in an appropriate construct. Inclusion body expression levels of ~75 mg/litre bacterial culture were obtained. The MHC light-chain or β2-microglobulin was also expressed as inclusion bodies in E. coli from an appropriate construct, at a level of ~500 mg/litre bacterial culture.

E. coli cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/litre heavy chain, 30 mg/litre β2m into 0.4 M L-Arginine, 100 mM Tris pH 8.1, 3.7 mM cystamine dihydrochloride, 6.6 mM cysteamine hydrochloride, 4 mg/L of the MAGE-A4 GVYDGREHTV (SEQ ID NO: 1) or MAGE-B2 GVYDGEEHSV (SEQ ID NO: 1) peptide required to be loaded by the HLA-A*02 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 m cellulose acetate filter and loaded onto a POROS 50HQ anion exchange column (8 ml bed volume). Protein was eluted with a linear 0-500 mM NaCl gradient in 10 mM Tris pH 8.1 using an Akta purifier (GE Healthcare). HLA-A*0201-peptide complex eluted at approximately 250 mM NaCl, and peak fractions were collected, a cocktail of protease inhibitors (Calbiochem) was added and the fractions were chilled on ice.

Biotin-tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM $MgCl_2$, and 5 µg/ml BirA enzyme (purified according to O'Callaghan et al. (1999) *Anal. Biochem.* 266: 9-15). The mixture was then allowed to incubate at room temperature overnight.

The biotinylated pHLA-A*0201 molecules were purified using gel filtration chromatography. A GE Healthcare Superdex 75 HR 10/30 column was pre-equilibrated with filtered PBS and 1 ml of the biotinylation reaction mixture was loaded and the column was developed with PBS at 0.5 ml/min using an Akta purifier (GE Healthcare). Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*01 molecules were stored frozen at −20° C.

Such immobilised complexes are capable of binding both T-cell receptors and the coreceptor CD8αα, both of which may be injected in the soluble phase. The pHLA binding properties of soluble TCRs are observed to be qualitatively and quantitatively similar if the TCR is used either in the soluble or immobilised phase. This is an important control for partial activity of soluble species and also suggests that biotinylated pHLA complexes are biologically as active as non-biotinylated complexes.

The BIAcore 3000™ surface plasmon resonance (SPR) biosensor measures changes in refractive index expressed in response units (RU) near a sensor surface within a small flow cell, a principle that can be used to detect receptor ligand interactions and to analyse their affinity and kinetic parameters. The BIAcore experiments were performed at a temperature of 25° C., using PBS buffer (Sigma, pH 7.1-7.5) as the running buffer and in preparing dilutions of protein samples. Streptavidin was immobilised to the flow cells by standard amine coupling methods. The pHLA complexes were immobilized via the biotin tag. The assay was then performed by passing soluble TCR over the surfaces of the different flow cells at a constant flow rate, measuring the SPR response in doing so.

Equilibrium Binding Constant

The above BIAcore analysis methods were used to determine equilibrium binding constants. Serial dilutions of the disulfide linked soluble heterodimeric form of the reference MAGE-A4 TCR were prepared and injected at constant flow rate of 5 µl min$^{-1}$ over two different flow cells; one coated with ~1000 RU of specific GVYDGREHTV (SEQ ID NO: 1) HLA-A*0201 complex, the second coated with ~1000 RU of non-specific complex. Response was normalised for each concentration using the measurement from the control cell. Normalised data response was plotted versus concentration of TCR sample and fitted to a non-linear curve fitting model in order to calculate the equilibrium binding constant, $K_D$. (Price & Dwek, Principles and Problems in Physical Chemistry for Biochemists (2$^{nd}$ Edition) 1979, Clarendon Press, Oxford). The disulfide linked soluble form of the reference MAGE-A4 TCR (Example 2) demonstrated a $K_D$ of approximately 2.00 µM. From the same BIAcore data the T½ was approximately 0.95 s.

Kinetic Parameters

The above BIAcore analysis methods were also used to determine equilibrium binding constants and off-rates.

For high affinity TCRs (see Example 4 below) $K_D$ was determined by experimentally measuring the dissociation rate constant, $k_{off}$, and the association rate constant, $k_{on}$. The equilibrium constant $K_D$ was calculated as $k_{off}/k_{on}$.

TCR was injected over two different cells one coated with ~1000 RU of specific GVYDGREHTV (SEQ ID NO: 1) HLA-A*0201complex, the second coated with ~1000 RU of non-specific complex. Flow rate was set at 50 µl/min. Typically 250 µl of TCR at ~1 µM concentration was injected. Buffer was then flowed over until the response had returned to baseline or >2 hours had elapsed. Kinetic parameters were calculated using BIAevaluation software. The dissociation phase was fitted to a single exponential decay equation enabling calculation of half-life.

Example 4—Preparation of High Affinity TCRs of the Invention

Expression plasmids containing the TCR α-chain and β-chain respectively were prepared as in Example 1:

| TCR ID | Alpha Chain SEQ ID NO: | Beta Chain SEQ ID NO: |
|---|---|---|
| TCR1 (parental) | 3 | 4 |
| TCR2 | 3 | 9 |
| TCR3 | 7 | 9 |
| TCR4 | 8 | 9 |

The plasmids were transformed separately into *E. coli* strain BL21pLysS, and single ampicillin-resistant colonies grown at 37° C. in TYP (ampicillin 100 µg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (Novagen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 10 mg of TCR α chain and 10 mg of TCR β chain solubilised inclusion bodies for each TCR of the invention were diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectrapor 1 membrane (Spectrum; Product No. 132670) against 10 L H₂O for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS 50HQ anion exchange column and eluting bound protein with a gradient of 0-500 mM NaCl in 10 mM Tris pH 8.1 over 15 column volumes using an Akta purifier (GE Healthcare). The pooled fractions were then stored at 4° C. and analysed by Coomassie-stained SDS-PAGE before being pooled and concentrated. Finally, the soluble TCRs were purified and characterised using a GE Healthcare Superdex 75HR gel filtration column pre-equilibrated in PBS buffer (Sigma). The peak eluting at a relative molecular weight of approximately 50 kDa was pooled and concentrated prior to characterization by BIAcore surface plasmon resonance analysis.

The affinity profiles of the thus-prepared TCRs for the MAGE-A4 epitope or MAGE-B2 epitope were assessed using the method of Example 3, and compared with the reference TCR. The results are set forth in the following table:

|  | MAGE A4 $K_D$ (μM) | MAGE-B2 $K_D$ (μM) |
| --- | --- | --- |
| Reference (TCR1) | 65.1 | 17 |
| TCR2 | 17.2 | 197.5 |
| TCR3 | 2.6 | 27.6 |
| TCR4 | 5.1 | 52.6 |

Attempts were also made to prepare high affinity TCRs based on combinations of SEQ ID Nos 10/11, 12/13, 14/15.

In the case of TCR A, which combines alpha chain of SEQ ID NO: 10 and the Beta chain of SEQ ID NO: 11, cross-reactivity was noted between MAGE-A1, MAGE-A10 and PRAME. It was not possible to remove this cross-reactivity by mutation and selection.

TCR B combines the alpha chain of SEQ ID NO: 12 and the Beta chain of SEQ ID NO: 13. TCR B could not be folded to form a soluble TCR, so no binding characterisation was possible.

TCR C combines the alpha chain of SEQ ID NO: 14 and the Beta chain of SEQ ID NO: 15. This TCR was soluble when expressed and could bid to antigen. However, when expressed in T-cells, TCR C showed no activity.

Example 5—Transfection of T-cells with Parental and Variant MAGE-A4 TCRs (a) Lentiviral Vector Preparation by Express-In Mediated Transient Transfection of 293T Cells A 3rd generation lentiviral packaging system was used to package lentiviral vectors containing the gene encoding the desired TCR. 293T cells were transfected with 4 plasmids (one lentiviral vector containing the TCR alpha chain-P2A-TCR beta chain single ORF gene described in Example 5c (below), and 3 plasmids containing the other components necessary to construct infective but non-replicative lentiviral particles) using Express-In mediated transfection (Open Biosystems).

For transfection one T150 flask of 293T cells in exponential growth phase was taken, with cells evenly distributed on the plate, and slightly more than 50% confluent. Express-In aliquots were brought to room temperature. 3 ml Serum-Free Medium (RPMI 1640+10 mM HEPES) were placed in a sterile 15 ml conical tube. 174 μl of Express-In Reagent were added directly into the Serum-Free Medium (this provides for a 3.6:1 weight ratio of Reagent to DNA). This was mixed thoroughly by inverting tubes 3-4 times and incubated at room temperature for 5-20 minutes.

In a separate 1.5 ml microtube was added 15 μg plasmid DNA to premixed packaging mix aliquots (containing 18 μg pRSV.REV (Rev expression plasmid), 18 μg pMDLg/p.RRE (Gag/Pol expression plasmid), 7 μg pVSV-G (VSV glycoprotein expression plasmid), usually ~22 μl, and pipetted up and down to ensure homogeneity of the DNA mix. Approx 1 mL of Express-In/Serum-Free Medium was added to the DNA mix dropwise then pipetted up and down gently before transferring back to the remainder of the Express-In/Serum-Free Medium. The tube was inverted tube 3-4 times and incubated at room temperature for 15-30 minutes. Old culture medium was removed from the flask of cells. Express-In/medium/DNA (3 mL) complex was added directly into the bottom of an upright flask of 293T cells. Slowly, the flask was placed flat to cover the cells and very gently rocked to ensure even distribution. After 1 minute 22 ml fresh culture medium (R10+HEPES: RPMI 1640, 10% heat-inactivated FBS, 1% Pen/Strep/L-glutamine, 10 mM HEPES) was added and the flask carefully returned to the incubator. This was incubated overnight at 37° C./5% CO2. After 24 hours, the medium containing packaged lentiviral vectors was harvested.

To harvest the packaged lentiviral vectors, the cell culture supernatant was filtered through a 0.45 micron nylon syringe filter, the culture medium centrifuged at 10,000 g for 18 hours (or 112,000 g for 2 hours), most of the supernatant removed (taking care not to disturb the pellet) and the pellet resuspended in the remaining few mL of supernatant (usually about 2 ml from a 31 ml starting volume per tube). This was snap frozen on dry ice in 1 ml aliquots and stored at −80° C.

(b) Transduction of T cells with Packaged Lentiviral Vectors Containing Gene of Interest Prior to transduction with the packaged lentiviral vectors, human T cells (CD8 or CD4 or both depending on requirements) were isolated from the blood of healthy volunteers. These cells were counted and incubated overnight in R10 containing 50 U/mL IL-2 at 1×10⁶ cells per ml (0.5 mL/well) in 48 well plates with pre-washed anti-CD3/CD28 antibody-coated microbeads (Dynabeads® T cell expander, Invitrogen) at a ratio of 3 beads per cell.

After overnight stimulation, 0.5 ml of neat packaged lentiviral vector was added to the desired cells. This was incubated at 37° C./5% CO2 for 3 days. 3 days post-transduction the cells were counted and diluted to 0.5×10⁶ cells/ml. Fresh medium containing IL-2 was added as required. Beads were removed 5-7 days post-transduction. Cells were counted and fresh medium containing IL-2 replaced or added at 2 day intervals. Cells were kept between 0.5×10⁶ and 1×10⁶ cells/mL. Cells were analysed by flow cytometry from day 3 and used for functional assays (e.g. ELISpot for IFNγ release, see Example 6) from day 5. From day 10, or when cells are slowing division and reduced in size, cells are frozen in aliquots of at least 4×10⁶ cells/vial (at 1×10⁷ cells/ml in 90% FBS/10% DMSO) for storage.

Example 6—Activation of MAGE A4 TCR Engineered T Cells

The following assay was carried out to demonstrate the activation of TCR-transduced cytotoxic T lymphocytes (CTLs) in response to tumour cell lines. IFN-7 production, as measured using the ELISPOT assay, was used as a read-out for cytotoxic T lymphocyte (CTL) activation.

ELISPOTs

Reagents

Assay media: 10% FCS (Gibco, Cat #2011-09), 88% RPMI 1640 (Gibco, Cat #42401), 1% glutamine (Gibco Cat #25030) and 1% penicillin/streptomycin (Gibco Cat #15070-063).

Wash buffer: 0.01M PBS/0.05% Tween 20

PBS (Gibco Cat #10010)

The Human IFNγ ELISPOT kit (BD Bioscience; Cat #551849) containing capture and detection antibodies and Human IFN-7 PVDF ELISPOT 96 well plates, with associated AEC substrate set (BD Bioscience, Cat #551951)

Methods

Target Cell Preparation

The target cells used in this method were natural epitope-presenting cells: A375 human melanoma cells which are both HLA-A2$^+$ MAGE A10$^+$. HCT116 human colon cancer, which are HLA-A2$^+$ MAGE A10$^-$, were used as a negative control. Sufficient target cells (50,000 cells/well) were washed by centrifugation three times at 1200 rpm, 10 min in a Megafuge® 1.0 (Heraeus). Cells were then re-suspended in assay media at $10^6$ cells/ml.

Effector Cell Preparation

The effector cells (T cells) used in this method were peripheral blood lymphocytes (PBL), obtained by negative selection using CD14 and CD25 microbead kits (Miltenyi Biotech Cat #130-050-201 and 130-092-983 respectively) from freshly isolated peripheral blood mononuclear cells (PBMC) from the venous blood of healthy volunteers. Cells were stimulated with antiCD3/CD28 coated beads (Dynabeads® T cell expander, Invitrogen), transduced with lentivirus carrying the gene encoding the full αβ TCR of interest (based on the construct described in Example 5) and expanded in assay media containing 50 U/mL IL-2 until between 10 and 13 days post transduction. These cells were then placed in assay media prior to washing by centrifugation at 1200 rpm, 10 min in a Megafuge® 1.0 (Heraeus). Cells were then re-suspended in assay media at a 4× the final required concentration.

Plates were prepared as follows: 100 µL anti-IFN-7 capture antibody was diluted in 10 ml sterile PBS per plate. 100 µL of the diluted capture antibody was then dispensed into each well. The plates were then incubated overnight at 4° C. Following incubation the plates were washed (programme 1, plate type 2, Ultrawash Plus 96-well plate washer; Dynex) to remove the capture antibody. Plates were then blocked by adding 200 µL of assay media to each well and incubated at room temperature for two hours. The assay media was then washed from the plates (programme 1, plate type 2, Ultrawash Plus 96-well plate washer, Dynex) and any remaining media was removed by flicking and tapping the ELISPOT plates on a paper towel.

The constituents of the assay were then added to the ELISPOT plate in the following order:

50 µL of target cells $10^6$ cells/ml (giving a total of 50,000 target cells/well)

50 µL media (assay media)

50 µL effector cells (20,000 TCR–transduced PBL cells/well)

The plates were then incubated overnight (37° C./5% $CO_2$). The next day the plates were washed three times (programme 1, plate type 2, Ultrawash Plus 96-well plate washer, Dynex) with wash buffer and tapped dry on paper towel to remove excess wash buffer. 100 µl of primary detection antibody was then added to each well. The primary detection antibody was diluted into 10 mL of dilution buffer (the volume required for a single plate) using the dilution specified in the manufacturer's instructions. Plates were then incubated at room temperature for at least 2 hours prior to being washed three times (programme 1, plate type 2, Ultrawash Plus 96-well plate washer, Dynex) with wash buffer; excess wash buffer was removed by tapping the plate on a paper towel.

Secondary detection was performed by adding 100 µL of diluted streptavidin-HRP to each well and incubating the plate at room temperature for 1 hour. The streptavidin-HRP was diluted into 10 mL dilution buffer (the volume required for a single plate), using the dilution specified in the manufacturer's instructions. The plates were then washed three times (programme 1, plate type 2, Ultrawash Plus 96-well plate washer, Dynex) with wash buffer and tapped on paper towel to remove excess wash buffer. Plates were then washed twice with PBS by adding 200 µL to each well, flicking the buffer off and tapping on a paper towel to remove excess buffer. No more than 15 min prior to use, one drop (20 µL) of AEC chromogen was added to each 1 ml of AEC substrate and mixed. 10 ml of this solution was prepared for each plate; 100 µL was added per well. The plate was then protected from light using foil, and spot development monitored regularly, usually occurring within 5-20 min. The plates were washed in tap water to terminate the development reaction, and shaken dry prior to their disassembly into three constituent parts. The plates were then allowed to dry at room temperature for at least 2 hours prior to counting the spots using an Immunospot® Plate reader (CTL; Cellular Technology Limited).

Example 7—Identification of the Binding Motif by Substitution with All Alternative Amino Acids Variants of the native MAGE-A4 peptide were obtained in which the amino acid residue at each position was sequentially replaced with all 19 alternative naturally-occurring amino acid, such that 171 peptides were prepared in total. The native and amino-acid substituted peptides were pulsed on to antigen presenting cells, and interferon γ (IFNγ) production, as measured using the ELISpot assay, used as a read-out for the activation of T cells transduced with TCR4. Essential positions were defined by a greater than 50% reduction in T cell activity relative to the native peptide.

ELISpot assays were carried as described in Example 6.

The tolerated residues at each position of the peptide are shown below. Underlined amino acids represent the native residue at the corresponding position in the peptide.

| Position | Tolerated residues |
| --- | --- |
| 1 | G, H |
| 2 | V, I, L |
| 3 | Y, V, F |
| 4 | D, N |
| 5 | G, N |
| 6 | K, A, R, G, S, C, H, T, Q, M, F, V, N, L, Y, I |
| 7 | S, H, Q, M, E, I, L, W, P, Y, F, A, T, C, N, D, G, R, K, V |

-continued

| Position | Tolerated residues |
|---|---|
| 8 | D, S, H, Q, M, E̲, I, L, W, P, Y, F, A, T, C, N, G, R, K, V |
| 9 | S, H̲, Q, M, E, I, L, W, P, Y, F, A, T, C, N, D, G, R, K, V |
| 10 | V̲, F, M, A, I, L, T |

It is therefore apparent that the MAGE A4 TCR4 makes contact with at least V2 Y3 and D4 of the peptide (SEQ ID NO: 1) when in complex with HLA-A*0201 on the surface of antigen presenting cells.

The invention is further described by the following numbered paragraphs:

1. A T cell receptor (TCR) having the property of binding to GVYDGREHTV (SEQ ID NO: 1) in complex with HLA-A*0201 with a dissociation constant of from about 0.05 to about 20.0 µM when measured with surface plasmon resonance at 25° C. and at a pH between 7.1 and 7.5 using a soluble form of the TCR, and has at least a ten-fold selectivity of binding to SEQ ID NO:1 in complex with HLA-A*0201 over binding to GVYDGAYVSV (SEQ ID NO: 2) in complex with HLA-A*0201 wherein the TCR comprises a TCR alpha chain variable domain and a TCR beta chain variable domain, and wherein the TCR variable domains form contacts with at least residues V2, Y3 and D4 of GVDGKSDSV (SEQ ID NO: 1).

2. A TCR according to numbered paragraph 1, which is an alpha-beta heterodimer, having an alpha chain TRAV10+TRAC constant domain sequence and a beta chain TRBV24-1+TRBC-2 constant domain sequence.

3. A TCR as claimed in numbered paragraph 1, which is in single chain format of the type Vα-L-Vβ, Vβ-L-Vα, Vα-Cα-L-Vβ, or Vα-L-Vβ-Cβ, wherein Vα and Vβ are TCR α and β variable regions respectively, Cα and Cβ are TCR α and β constant regions respectively, and L is a linker sequence.

4. A TCR as claimed in any preceding numbered paragraph, which is associated with a detectable label, a therapeutic agent or a PK modifying moiety.

5. A TCR as claimed in any preceding numbered paragraph, wherein the alpha chain variable domain comprises an amino acid sequence that has at least 80% identity to the sequence of amino acid residues 1-105 of SEQ ID NO: 3 and has the following mutation:

| M51 | V or L |
|---|---| with reference to the numbering shown in SEQ ID NO: 3, and/or the beta chain variable domain comprises an amino acid sequence that has at least 80% identity to the sequence of amino acid residues 1-105 of SEQ ID NO: 4 and has at least one of the following mutations:

| N119 | E |
|---|---| with reference to the numbering shown in SEQ ID NO: 4.

6. A TCR as claimed in any preceding numbered paragraph, wherein the alpha chain variable domain comprises the amino acid sequence of amino acid residues 1-105 of SEQ ID NO: 3 or 5 or 7 to 8 or
an amino acid sequence in which amino acid residues 1-27, 34-47, and 54-90 thereof have at least 90% or 95% identity to the sequence of amino acid residues 1-27, 34-47, and 54-90 respectively of SEQ ID NO: 3 or 5 or 7 to 8 and in which amino acid residues 28-33, 48-53 and 91-105 have at least 90% or 95% identity to the sequence of amino acid residues 28-33, 48-53 and 91-105 respectively of SEQ ID NO: 3 or 5 or 7 to 8.

7. A TCR as claimed in any one of numbered paragraphs 1-7, wherein the alpha chain variable domain comprises the amino acid sequence of amino acid residues 1-105 of SEQ ID NO: 7 or 8 or an amino acid sequence in which amino acid residues 1-27, 34-47 and 54-90 thereof have at least 90% or 95% identity to the sequence of amino acid residues 1-27, 34-47, and 54-90 respectively of SEQ ID NO: 7 or 8 and in which amino acid residues 28-33, 48-53 and 91-105 have at least 90% or 95% identity to the sequence of amino acid residues 28-33, 48-53 and 91-105 respectively of SEQ ID NO: 7 or 8.

8. A TCR as claimed in any preceding numbered paragraph, wherein in the alpha chain variable domain the sequence of
  (i) amino acid residues 1-27 thereof has (a) at least 90% identity to the sequence of amino acid residues 1-27 of SEQ ID NO: 3 or (b) has one, two or three amino acid residues inserted or deleted relative to the sequence of (a);
  (ii) amino acid residues 28-33 of SEQ ID NO: 3;
  (iii) amino acid residues 34-47 thereof has (a) at least 90% identity to the sequence of amino acid residues 34-47 of SEQ ID NO: 3 or (b) has one, two or three amino acid residues inserted or deleted relative to the sequence of (a);
  (iv) amino acid residues 48-53 of SEO ID NO: 3 or amino acid residues 48-50, 52 and 53 of SEQ ID NO: 3 with amino acid residue 51 of SEQ ID NO: 3 substituted with β instead of I or amino acid residues 48-50, 52 and 53 of SEQ ID NO: 3 with amino acid residue 51 of SEQ ID NO: 3 substituted with V instead of I or amino acid residues 48-51 and 53 of SEQ ID NO: 3 with amino acid residue 52 of SEQ ID NO: 3 substituted with L instead of M;
  (v) amino acid residues 54-90 thereof has at least 90% identity to the sequence of amino acid residues 54-90 of SEQ ID NO: 3 or has one, two or three insertions, deletions or substitutions relative thereto;
  (vi) amino acids 91-105 of SEQ ID NO: 3.

9. A TCR as claimed in any preceding numbered paragraph, wherein the beta chain variable domain comprises the amino acid sequence of SEQ ID NO: 4 or 6 or 9 or an amino acid sequence in which amino acid residues 1-45, 51-67, and 73-109 thereof have at least 90% or 95% identity to the sequence of amino acid residues 1-45, 51-67, and 73-109 respectively of SEQ ID NO: 4 or 6 or 9 and in which amino acid residues 46-50, 68-72 and 110-123 have at least 90% or 95% identity to the sequence of amino acid residues 46-50, 68-72 and 110-123 respectively of SEQ ID NO: 4 or 6 or 9.

10. A TCR according to any preceding numbered paragraph, wherein in the beta chain variable domain the sequence of
  (i) amino acid residues 1-45 thereof has (a) at least 90% identity to the amino acid sequence of residues 1-45 of SEQ ID NO: 4 or (b) has one, two or three amino acid residues inserted or deleted relative to the sequence of (a);
  (ii) amino acid residues 46-50 of SEQ ID NO: 4;
  (iii) amino acid residues 51-67 thereof has (a) at least 90% identity to the sequence of amino acid residues 51-67 of SEQ ID NO: 4 or (b) has one, two or three amino acid residues inserted or deleted relative to the sequence of (a);

(iv) amino acid residues 68-72 of SEQ ID NO: 4;

(v) amino acid residues 73-109 thereof has (a) at least 90% identity to the sequence of amino acid residues 73-109 of SEQ ID NO: 4 or (b) has one, two or three amino acid residues inserted or deleted relative to the sequence of (a);

(vi) amino acid residues 110-123 of SEQ ID NO: 4 or amino acid residues 110-118 and 120-123 of SEQ ID NO: 4 with amino acid residue 119 of SEQ ID NO: 4 substituted with R instead of N.

11. Nucleic acid encoding a TCR as claimed in any one of the preceding numbered paragraphs.

12. An isolated or non-naturally occurring cell, especially a T-cell, presenting a TCR as claimed in any one of numbered paragraphs 1 to 11.

13. A cell harboring
(a) a TCR expression vector which comprises nucleic acid as claimed in numbered paragraph 12 in a single open reading frame, or two distinct open reading frames encoding the alpha chain and the beta chain respectively; or
(b) a first expression vector which comprises nucleic acid encoding the alpha chain of a TCR as claimed in any of numbered paragraphs 1 to 11, and a second expression vector which comprises nucleic acid encoding the beta chain of a TCR as claimed in any of numbered paragraphs 1 to 11.

14. A pharmaceutical composition comprising a TCR as claimed in any one of numbered paragraphs 1 to 10, nucleic acid of numbered paragraph 11 or a cell as claimed in numbered paragraph 12 or numbered paragraph 13, together with one or more pharmaceutically acceptable carriers or excipients.

15. The TCR of any one of numbered paragraphs 1 to 12, nucleic acid of numbered paragraph 13 or cell of numbered paragraph 14 or numbered paragraph 15 for use in medicine.

16. The TCR, nucleic acid or cell for use as claimed in numbered paragraph 15, for use in a method of treating cancer.

```
MAGE A4 Epitope
                                                    SEQ ID NO: 1
GVVDGREHTV MAGE B2 Epitope
                                                    SEQ ID NO: 2
GVYDGEEHSV alpha variable chain
                                                    SEQ ID NO: 3
MKNQVEQSPQSLIILEGKNCTLQCNYTVSPFSNLRWYKQDTGRGPVSLTIMTFSENTKSN

GRYTATLDADTKQSSLHITASQLSDSASYICVVSGGTDSWGKLQF beta variable chain
                                                    SEQ ID NO: 4
MASLLFFCGAFYLLGTGSMDADVTQTPRNRITKTGKRIMLECSQTKGHDRMYWYRQDP

GLGLRLIYYSFDVKDINKGEISDGYSVSRQAQAKFSLSLESAIPNQTALYFCATSGQGAY

NEQFF alpha chain soluble form
                                                    SEQ ID NO: 5
MKKHLTTFLVILWLYFYRGNGKNQVEQSPQSLIILEGKNCTLQCNYTVSPFSNLRWYKQ

DTGRGPVSLTIMTFSENTKSNGRYTATLDADTKQSSLHITASQLSDSASYICVVSGGTDS

WGKLQFGAGTQVVVTPDIQNPDPAVYQLRDSKSSDKSVCLFTDFDSQTNVSQSKDSDV

YITDKTVLDMRSMDFKSNSAVAWSNKSDFACANAFNNSIIPEDTFFPSPESS beta chain soluble form
                                                    SEQ ID NO: 6
MASLLFFCGAFYLLGTGSMDADVTQTPRNRITKTGKRIMLECSQTKGHDRMYWYRQDP

GLGLRLIYYSFDVKDINKGEISDGYSVSRQAQAKFSLSLESAIPNQTALYFCATSGQGAY

NEQFFGPGTRLTVLEDLKNVFPPEVAVFEPSEAEISHTQKATLVCLATGFYPDHVELSW

WVNGKEVHSGVSTDPQPLKEQPALNDSRYCLSSRLRVSATFWQNPRNHFRCQVQFYGL

SENDEWTQDRAKPVTQIVSAEAWGRAD mutant alpha variable chain
                                                    SEQ ID NO: 7
MKNQVEQSPQSLIILEGKNCTLQCNYTVSPFSNLRWYKQDTGRGPVSLTIVTFSENTKSN

GRYTATLDADTKQSSLHITASQLSDSASYICVVSGGTDSWGKLQF mutant alpha variable chain
                                                    SEQ ID NO: 8
MKNQVEQSPQSLIILEGKNCTLQCNYTVSPFSNLRWYKQDTGRGPVSLTILTFSENTKSN
```

-continued

GRYTATLDADTKQSSLHITASQLSDSASYI<u>CVVSGGTDSWGKLQF</u> mutant beta variable chain
 SEQ ID NO: 9
MASLLFFCGAFYLLGTGSMDADVTQTPRNRITKTGKRIMLECSQT<u>KGHDR</u>MYWYRQDP GLGLRLIYY<u>SFDVK</u>DINKGEISDGYSVSRQAQAKFSLSLESAIPNQTALYF<u>CATSGQGAY</u>

<u>EE</u>QFF alpha chain soluble form
 SEQ ID NO: 10
METLLGLLILWLQLQWVSSKQEVTQIPAALSVPEGENLVLNCSFTDSAIYNLQWFRQDP

GKGLTSLLLIQSSQREQTSGRLNASLDKSSGRSTLYIAASQPGDSATYLCAVGGYSTLTF

GKGTVLLVSPDNIQNPDPAVYQLRDSKSSDKSVCLFTDFDSQTNVSQSKDSDVYITDKT

VLDMRSMDFKSNSAVAWSNKSDFACANAFNNSIIPEDTFFPSPESSCDVKLVEKSFETDT

NLNFQNLSVIGFRILLLKVAGENLLMTLRLWSS beta chain soluble form
 SEQ ID NO: 11
MSISLLCCAAFPLLWAGPVNAGVTQTPKFRILKIGQSMTLQCAQDMNHNYMYWYRQD

PGMGLKLIYYSVGAGITDKGEVPNGYNVSRSTTEDFPLRLELAAPSQTSVYFCASSYSR

WSPLHFGNGTRLTVTEDLNKVFPPEVAVFEPSEAEISHTQKATLVCLATGFFPDHVELSW

WVNGKEVHSGVSTDPQPLKEQPALNDSRYCLSSRLRVSATFWQNPRNHFRCQVQFYGL

SENDEWTQDRAKPVTQIVSAEAWGRADCGFTSVSYQQGVLSATILYEILLGKATLYAVL

VSALVLMAMVKRKDF alpha chain soluble form
 SEQ ID NO: 12
MQKEVEQNSGPLSVPEGAIASLNCTYSDRGSQSFFWYRQYSGKSPELIMFIYSNGDKED

GRFTAQLNKASQYVSLLIRDSQPSDSATYLCAVKMANQAGTALIFGKGTTLSVSSNIQNP

DPAVYQLRDSKSSDKSVCLFTDFDSQTNVSQSKDSDVYITDKCVLDMRSMDFKSNSAV

AWSNKSDFACANAFNNSIIPEDTFFPSPESS beta chain soluble form
 SEQ ID NO: 13
MQDGGITQSPKFQVLRTGQSMTLLCAQDMNHEYMYWYRQDPGMGLRLIHYSVGAGIT

DQGEVPNGYNVSRLNKREFSLRLESAAPSQTSVYFCASLGGLADEQFFGPGTRLTVLED

LKNVFPPEVAVFEPSEAEISHTQKATLVCLATGFYPDHVELSWWVNGKEVHSGVCTDP

QPLKEQPALNDSRYALSSRLRVSATFWQDPRNHFRCQVQFYGLSENDEWTQDRAKPVT

QIVSAEAWGRAD alpha chain soluble form
 SEQ ID NO: 14
MKTFAGFSFLFLWLQLDCMSRGEDVEQSLFLSVREGDSSVINCTYTDSSSTYLYWYKQE

PGAGLQLLTYIFSNMDMKQDQRLTVLLNKKDKHLSLRIADTQTGDSAIYFCAERNSGAG

SYQLTFGKGTKLSVIPNIQNPDPAVYQLRDSKSSDKSVCLFTDFDSQTNVSQSKDSDVYI

TDKTVLDMRSMDFKSNSAVAWSNKSDFACANAFNNSIIPEDTFFPSPESSCDVKLVEKSF

ETDTNLNFQNLSVIGFRILLLKVAGFNLLMTLRLWSS beta chain soluble form
 SEQ ID NO: 15
MGTSLLCWMALCLLGADHADTGVSQNPRHKITKRGQNVTFRCDPISEHNRLYWYRQTL

GQGPEFLTYFQNEAQLEKSRLLSDRFSAERPKGSFSTLEIQRTEQGDSAMYLCASSLFSG

VNTEAFFGQGTRLTVVEDLNKVFPPEVAVFEPSEAEISHTQKATLVCLATGFFPDHVELS

WWVNGKEVHSGVSTDPQPLKEQPALNDSRYCLSSRLRVSATFWQNPRNHFRCQVQFY

GLSENDEWTQDRAKPVTQIVSAEAWGRADCGFTSVSYQQGVLSATILYEILLGKATLYA

VLVSALVLMAMVKRKDF

---

SEQUENCE LISTING

Sequence total quantity: 29
```
SEQ ID NO: 1            moltype = AA  length = 10
FEATURE                 Location/Qualifiers
source                  1..10
                        mol_type = protein
                        organism = Homo sapiens
SEQUENCE: 1
GVYDGREHTV                                                                       10

SEQ ID NO: 2            moltype = AA  length = 10
FEATURE                 Location/Qualifiers
source                  1..10
                        mol_type = protein
                        organism = Homo sapiens
SEQUENCE: 2
GVYDGEEHSV                                                                       10

SEQ ID NO: 3            moltype = AA  length = 105
FEATURE                 Location/Qualifiers
REGION                  1..105
                        note = source = /note="Description of Artificial Sequence:
                        Syntheticpolypeptide"
source                  1..105
                        mol_type = protein
                        organism = synthetic construct
SEQUENCE: 3
MKNQVEQSPQ SLIILEGKNC TLQCNYTVSP FSNLRWYKQD TGRGPVSLTI MTFSENTKSN                 60
GRYTATLDAD TKQSSLHITA SQLSDSASYI CVVSGGTDSW GKLQF                                105

SEQ ID NO: 4            moltype = AA  length = 123
FEATURE                 Location/Qualifiers
REGION                  1..123
                        note = source = /note="Description of Artificial Sequence:
                        Syntheticpolypeptide"
source                  1..123
                        mol_type = protein
                        organism = synthetic construct
SEQUENCE: 4
MASLLFFCGA FYLLGTGSMD ADVTQTPRNR ITKTGKRIML ECSQTKGHDR MYWYRQDPGL                 60
GLRLIYYSFD VKDINKGEIS DGYSVSRQAQ AKFSLSLESA IPNQTALYFC ATSGQGAYNE                120
QFF                                                                             123

SEQ ID NO: 5            moltype = AA  length = 229
FEATURE                 Location/Qualifiers
REGION                  1..229
                        note = source = /note="Description of Artificial Sequence:
                        Syntheticpolypeptide"
source                  1..229
                        mol_type = protein
                        organism = synthetic construct
SEQUENCE: 5
MKKHLTTFLV ILWLYFYRGN GKNQVEQSPQ SLIILEGKNC TLQCNYTVSP FSNLRWYKQD                 60
TGRGPVSLTI MTFSENTKSN GRYTATLDAD TKQSSLHITA SQLSDSASYI CVVSGGTDSW                120
GKLQFGAGTQ VVVTPDIQNP DPAVYQLRDS KSSDKSVCLF TDFDSQTNVS QSKDSDVYIT                180
DKTVLDMRSM DFKSNSAVAW SNKSDFACAN AFNNSIIPED TFFPSPESS                            229

SEQ ID NO: 6            moltype = AA  length = 262
FEATURE                 Location/Qualifiers
REGION                  1..262
                        note = source = /note="Description of Artificial Sequence:
                        Syntheticpolypeptide"
source                  1..262
                        mol_type = protein
                        organism = synthetic construct
SEQUENCE: 6
MASLLFFCGA FYLLGTGSMD ADVTQTPRNR ITKTGKRIML ECSQTKGHDR MYWYRQDPGL                 60
GLRLIYYSFD VKDINKGEIS DGYSVSRQAQ AKFSLSLESA IPNQTALYFC ATSGQGAYNE                120
QFFGPGTRLT VLEDLKNVFP PEVAVFEPSE AEISHTQKAT LVCLATGFYP DHVELSWWVN                180
GKEVHSGVST DPQPLKEQPA LNDSRYCLSS RLRVSATFWQ NPRNHFRCQV QFYGLSENDE                240
WTQDRAKPVT QIVSAEAWGR AD                                                        262
```

```
SEQ ID NO: 7              moltype = AA  length = 105
FEATURE                   Location/Qualifiers
REGION                    1..105
                          note = source = /note="Description of Artificial Sequence:
                          Syntheticpolypeptide"
source                    1..105
                          mol_type = protein
                          organism = synthetic construct
SEQUENCE: 7
MKNQVEQSPQ SLIILEGKNC TLQCNYTVSP FSNLRWYKQD TGRGPVSLTI VTFSENTKSN  60
GRYTATLDAD TKQSSLHITA SQLSDSASYI CVVSGGTDSW GKLQF                 105

SEQ ID NO: 8              moltype = AA  length = 105
FEATURE                   Location/Qualifiers
REGION                    1..105
                          note = source = /note="Description of Artificial Sequence:
                          Syntheticpolypeptide"
source                    1..105
                          mol_type = protein
                          organism = synthetic construct
SEQUENCE: 8
MKNQVEQSPQ SLIILEGKNC TLQCNYTVSP FSNLRWYKQD TGRGPVSLTI LTFSENTKSN  60
GRYTATLDAD TKQSSLHITA SQLSDSASYI CVVSGGTDSW GKLQF                 105

SEQ ID NO: 9              moltype = AA  length = 123
FEATURE                   Location/Qualifiers
REGION                    1..123
                          note = source = /note="Description of Artificial Sequence:
                          Syntheticpolypeptide"
source                    1..123
                          mol_type = protein
                          organism = synthetic construct
SEQUENCE: 9
MASLLFFCGA FYLLGTGSMD ADVTQTPRNR ITKTGKRIML ECSQTKGHDR MYWYRQDPGL  60
GLRLIYYSFD VKDINKGEIS DGYSVSRQAQ AKFSLSLESA IPNQTALYFC ATSGQGAYEE 120
QFF                                                              123

SEQ ID NO: 10             moltype = AA  length = 271
FEATURE                   Location/Qualifiers
REGION                    1..271
                          note = source = /note="Description of Artificial Sequence:
                          Syntheticpolypeptide"
source                    1..271
                          mol_type = protein
                          organism = synthetic construct
SEQUENCE: 10
METLLGLLIL WLQLQWVSSK QEVTQIPAAL SVPEGENLVL NCSFTDSAIY NLQWFRQDPG  60
KGLTSLLLIQ SSQREQTSGR LNASLDKSSG RSTLYIAASQ PGDSATYLCA VGGYSTLTFG 120
KGTVLLVSPD NIQNPDPAVY QLRDSKSSDK SVCLFTDFDS QTNVSQSKDS DVYITDKTVL 180
DMRSMDFKSN SAVAWSNKSD FACANAFNNS IIPEDTFFPS PESSCDVKLV EKSFETDTNL 240
NFQNLSVIGF RILLLKVAGF NLLMTLRLWS S                                271

SEQ ID NO: 11             moltype = AA  length = 308
FEATURE                   Location/Qualifiers
REGION                    1..308
                          note = source = /note="Description of Artificial Sequence:
                          Syntheticpolypeptide"
source                    1..308
                          mol_type = protein
                          organism = synthetic construct
SEQUENCE: 11
MSISLLCCAA FPLLWAGPVN AGVTQTPKFR ILKIGQSMTL QCAQDMNHNY MYWYRQDPGM  60
GLKLIYYSVG AGITDKGEVP NGYNVSRSTT EDFPLRLELA APSQTSVYFC ASSYSRWSPL 120
HFGNGTRLTV TEDLNKVFPP EVAVFEPSEA EISHTQKATL VCLATGFFPD HVELSWWVNG 180
KEVHSGVSTD PQPLKEQPAL NDSRYCLSSR LRVSATFWQN PRNHFRCQVQ FYGLSENDEW 240
TQDRAKPVTQ IVSAEAWGRA DCGFTSVSYQ QGVLSATILY EILLGKATLY AVLVSALVLM 300
AMVKRKDF                                                         308

SEQ ID NO: 12             moltype = AA  length = 208
FEATURE                   Location/Qualifiers
REGION                    1..208
                          note = source = /note="Description of Artificial Sequence:
                          Syntheticpolypeptide"
source                    1..208
                          mol_type = protein
                          organism = synthetic construct
SEQUENCE: 12
MQKEVEQNSG PLSVPEGAIA SLNCTYSDRG SQSFFWYRQY SGKSPELIMF IYSNGDKEDG  60
```

```
RFTAQLNKAS QYVSLLIRDS QPSDSATYLC AVKMANQAGT ALIFGKGTTL SVSSNIQNPD    120
PAVYQLRDSK SSDKSVCLFT DFDSQTNVSQ SKDSDVYITD KCVLDMRSMD FKSNSAVAWS    180
NKSDFACANA FNNSIIPEDT FFPSPESS                                       208

SEQ ID NO: 13              moltype = AA   length = 244
FEATURE                    Location/Qualifiers
REGION                     1..244
                           note = source = /note="Description of Artificial Sequence:
                             Syntheticpolypeptide"
source                     1..244
                           mol_type = protein
                           organism = synthetic construct
SEQUENCE: 13
MQDGGITQSP KFQVLRTGQS MTLLCAQDMN HEYMYWYRQD PGMGLRLIHY SVGAGITDQG    60
EVPNGYNVSR LNKREFSLRL ESAAPSQTSV YFCASLGGLA DEQFFGPGTR LTVLEDLKNV    120
FPPEVAVFEP SEAEISHTQK ATLVCLATGF YPDHVELSWW VNGKEVHSGV CTDPQPLKEQ    180
PALNDSRYAL SSRLRVSATF WQDPRNHFRC QVQFYGLSEN DEWTQDRAKP VTQIVSAEAW    240
GRAD                                                                 244

SEQ ID NO: 14              moltype = AA   length = 275
FEATURE                    Location/Qualifiers
REGION                     1..275
                           note = source = /note="Description of Artificial Sequence:
                             Syntheticpolypeptide"
source                     1..275
                           mol_type = protein
                           organism = synthetic construct
SEQUENCE: 14
MKTFAGFSFL FLWLQLDCMS RGEDVEQSLF LSVREGDSSV INCTYTDSSS TYLYWYKQEP    60
GAGLQLLTYI FSNMDMKQDQ RLTVLLNKKD KHLSLRIADT QTGDSAIYFC AERNSGAGSY    120
QLTFGKGTKL SVIPNIQNPD PAVYQLRDSK SSDKSVCLFT DFDSQTNVSQ SKDSDVYITD    180
KTVLDMRSMD FKSNSAVAWS NKSDFACANA FNNSIIPEDT FFPSPESSCD VKLVEKSFET    240
DTNLNFQNLS VIGFRILLLK VAGFNLLMTL RLWSS                               275

SEQ ID NO: 15              moltype = AA   length = 311
FEATURE                    Location/Qualifiers
REGION                     1..311
                           note = source = /note="Description of Artificial Sequence:
                             Syntheticpolypeptide"
source                     1..311
                           mol_type = protein
                           organism = synthetic construct
SEQUENCE: 15
MGTSLLCWMA LCLLGADHAD TGVSQNPRHK ITKRGQNVTF RCDPISEHNR LYWYRQTLGQ    60
GPEFLTYFQN EAQLEKSRLL SDRFSAERPK GSFSTLEIQR TEQGDSAMYL CASSLFSGVN    120
TEAFFGQGTR LTVVEDLNKV FPPEVAVFEP SEAEISHTQK ATLVCLATGF FPDHVELSWW    180
VNGKEVHSGV STDPQPLKEQ PALNDSRYCL SSRLRVSATF WQPRNHFRC QVQFYGLSEN     240
DEWTQDRAKP VTQIVSAEAW GRADCGFTSV SYQQGVLSAT ILYEILLGKA TLYAVLVSAL   300
VLMAMVKRKD F                                                         311

SEQ ID NO: 16              moltype = AA   length = 10
FEATURE                    Location/Qualifiers
source                     1..10
                           mol_type = protein
                           organism = Homo sapiens
SEQUENCE: 16
GVVDGREHTV                                                           10

SEQ ID NO: 17              moltype = AA   length = 10
FEATURE                    Location/Qualifiers
source                     1..10
                           mol_type = protein
                           organism = Homo sapiens
SEQUENCE: 17
GVYDGAYVSV                                                           10

SEQ ID NO: 18              moltype = AA   length = 6
FEATURE                    Location/Qualifiers
REGION                     1..6
                           note = source = /note="Description of Artificial Sequence:
                             Syntheticpeptide"
source                     1..6
                           mol_type = protein
                           organism = synthetic construct
SEQUENCE: 18
VSPFSN                                                               6

SEQ ID NO: 19              moltype = AA   length = 6
FEATURE                    Location/Qualifiers
```

```
                          -continued

REGION                    1..6
                          note = source = /note="Description of Artificial Sequence:
                           Syntheticpeptide"
source                    1..6
                          mol_type = protein
                          organism = synthetic construct
SEQUENCE: 19
LTIMTF                                                                            6

SEQ ID NO: 20             moltype = AA  length = 6
FEATURE                   Location/Qualifiers
REGION                    1..6
                          note = source = /note="Description of Artificial Sequence:
                           Syntheticpeptide"
source                    1..6
                          mol_type = protein
                          organism = synthetic construct
SEQUENCE: 20
LTRMTF                                                                            6

SEQ ID NO: 21             moltype = AA  length = 6
FEATURE                   Location/Qualifiers
REGION                    1..6
                          note = source = /note="Description of Artificial Sequence:
                           Syntheticpeptide"
source                    1..6
                          mol_type = protein
                          organism = synthetic construct
SEQUENCE: 21
LTIVTF                                                                            6

SEQ ID NO: 22             moltype = AA  length = 6
FEATURE                   Location/Qualifiers
REGION                    1..6
                          note = source = /note="Description of Artificial Sequence:
                           Syntheticpeptide"
source                    1..6
                          mol_type = protein
                          organism = synthetic construct
SEQUENCE: 22
LTILTF                                                                            6

SEQ ID NO: 23             moltype = AA  length = 15
FEATURE                   Location/Qualifiers
REGION                    1..15
                          note = source = /note="Description of Artificial Sequence:
                           Syntheticpeptide"
source                    1..15
                          mol_type = protein
                          organism = synthetic construct
SEQUENCE: 23
CVVSGGTDSW GKLQF                                                                 15

SEQ ID NO: 24             moltype = AA  length = 5
FEATURE                   Location/Qualifiers
REGION                    1..5
                          note = source = /note="Description of Artificial Sequence:
                           Syntheticpeptide"
source                    1..5
                          mol_type = protein
                          organism = synthetic construct
SEQUENCE: 24
KGHDR                                                                             5

SEQ ID NO: 25             moltype = AA  length = 5
FEATURE                   Location/Qualifiers
REGION                    1..5
                          note = source = /note="Description of Artificial Sequence:
                           Syntheticpeptide"
source                    1..5
                          mol_type = protein
                          organism = synthetic construct
SEQUENCE: 25
SVFDK                                                                             5

SEQ ID NO: 26             moltype = AA  length = 14
FEATURE                   Location/Qualifiers
REGION                    1..14
                          note = source = /note="Description of Artificial Sequence:
```

```
                        Syntheticpeptide"
source                  1..14
                        mol_type = protein
                        organism = synthetic construct
SEQUENCE: 26
CATSGQGAYN EQFF                                                              14

SEQ ID NO: 27           moltype = AA   length = 14
FEATURE                 Location/Qualifiers
REGION                  1..14
                        note = source = /note="Description of Artificial Sequence:
                        Syntheticpeptide"
source                  1..14
                        mol_type = protein
                        organism = synthetic construct
SEQUENCE: 27
CATSGQGAYR EQFF                                                              14

SEQ ID NO: 28           moltype = AA   length = 9
FEATURE                 Location/Qualifiers
source                  1..9
                        mol_type = protein
                        organism = Homo sapiens
SEQUENCE: 28
GVDGKSDSV                                                                     9

SEQ ID NO: 29           moltype = AA   length = 5
FEATURE                 Location/Qualifiers
REGION                  1..5
                        note = source = /note="Description of Artificial Sequence:
                        Syntheticpeptide"
source                  1..5
                        mol_type = protein
                        organism = synthetic construct
SEQUENCE: 29
SFDVK                                                                         5
```

The invention claimed is:

1. A T cell receptor (TCR) that comprises a TCR alpha chain variable domain and a TCR beta chain variable domain, wherein:
   (A) the TCR alpha chain variable domain is comprised in a sequence in which:
      (i) amino acid residues 1-27 has (a) at least 90% identity to the sequence of amino acid residues 1-27 of SEQ ID NO: 3 or (b) one, two or three amino acid insertions, deletions or substitutions relative to amino acid residues 1-27 of SEQ ID NO: 3;
      (ii) amino acid residues 28-33 is amino acid residues 28-33 of SEQ ID NO: 3;
      (iii) amino acid residues 34-47 has (a) at least 90% identity to the sequence of amino acid residues 34-47 of SEQ ID NO: 3 or (b) one, two or three amino acid insertions, deletions or substitutions relative to amino acid residues 34-47 of SEQ ID No: 3;
      (iv) amino acid residues 48-53 is amino acid residues 48-53 of any of one of SEQ ID NOs: 3, 7 or 8;
      (v) amino acid residues 54-90 has (a) at least 90% identity to the sequence of amino acid residues 54-90 of SEQ ID NO: 3 or (b) one, two or three amino acid insertions, deletions or substitutions relative to amino acid residues 54-90 of SEQ ID No: 3; and
      (vi) amino acid residues 91-105 is amino acid residues 91-105 of SEQ ID NO: 3; and
   (B) the TCR beta chain variable domain is comprised in a sequence in which:
      (i) amino acid residues 1-45 has (a) at least 90% identity to the amino acid sequence of residues 1-45 of SEQ ID NO: 4 or (b) one, two or three amino acid insertions, deletions or substitutions relative to amino acid residues 1-45 of SEQ ID NO: 4;
      (ii) amino acid residues 46-50 is amino acid residues 46-50 of SEQ ID NO: 9;
      (iii) amino acid residues 51-67 has (a) at least 90% identity to the sequence of amino acid residues 51-67 of SEQ ID NO: 4 or (b) one, two or three amino acid insertions, deletions or substitutions relative to amino acid residues 51-67 of SEQ ID NO: 4;
      (iv) amino acid residues 68-72 is amino acid residues 68-72 of SEQ ID NO: 9;
      (v) amino acid residues 73-109 has (a) at least 90% identity to the sequence of amino acid residues 73-109 of SEQ ID NO: 4 or (b) one, two or three amino acid insertions, deletions or substitutions relative to amino acid residues 73-109 of SEQ ID No: 4; and
      (vi) amino acid residues 110-123 is amino acid residues 110-123 of SEQ ID NO: 9.

2. The TCR of claim 1, wherein the TCR alpha chain variable domain is comprised in the amino acid sequence of SEQ ID NO: 3, 7 or 8.

3. The TCR of claim 1, wherein the TCR beta chain variable domain is comprised in the amino acid sequence of SEQ ID NO 9.

4. The TCR of claim 1, wherein the TCR alpha chain variable domain is comprised in the amino acid sequence of SEQ ID NO: 3, 7 or 8, and the TCR beta chain variable domain is comprised in the amino acid sequence of SEQ ID NO 9.

5. The TCR of claim 1, wherein the TCR alpha chain variable domain is comprised in the amino acid sequence of SEQ ID NO: 3, and the TCR beta chain variable domain is comprised in the amino acid sequence of SEQ ID NO 9.

6. The TCR of claim 1, wherein the TCR alpha chain variable domain is comprised in the amino acid sequence of SEQ ID NO: 7, and the TCR beta chain variable domain is comprised in the amino acid sequence of SEQ ID NO 9.

7. The TCR of claim 1, wherein the TCR alpha chain variable domain is comprised in the amino acid sequence of SEQ ID NO: 8, and the TCR beta chain variable domain is comprised in the amino acid sequence of SEQ ID NO 9.

8. One or more polynucleotides encoding the TCR of claim 7.

9. A cell comprising the one or more polynucleotides of claim 8.

10. A cell presenting the TCR of claim 7, optionally wherein the cell is isolated or non-naturally occurring.

11. The cell of claim 10, wherein the cell is a T-cell.

12. A method for treating cancer in a subject, comprising administering to the subject the T cell of claim 11, wherein the subject has a cancer cell that expresses a melanoma-associated antigen (MAGE) A4 protein.

13. A pharmaceutical composition comprising the cell of claim 10, together with one or more pharmaceutically acceptable carriers or excipients.

14. The TCR of claim 1, which is an alpha-beta heterodimer, having an alpha chain TRAV10+TRAC constant domain sequence and a beta chain TRBV24-1+TRBC-2 constant domain sequence.

15. The TCR of claim 1, which is in single chain format of the type Vα-L-Vβ, Vβ-L-Vα, Vα-Cα-L-Vβ, or Vα-L-Vβ-Cβ, wherein Vα and Vβ are TCR α and β variable regions respectively, Cα and Cβ are TCR α and β constant regions respectively, and L is a linker sequence.

16. One or more polynucleotides encoding the TCR of claim 1.

17. A cell comprising the one or more polynucleotides of claim 16.

18. A cell presenting the TCR of claim 1, optionally wherein the cell is isolated or non-naturally occurring.

19. The cell of claim 18, wherein the cell is a T-cell.

20. A method for treating cancer in a subject, comprising administering to the subject the T cell of claim 19, wherein the subject has a cancer cell that expresses a melanoma-associated antigen (MAGE) A4 protein.

21. A pharmaceutical composition comprising the cell of claim 18, together with one or more pharmaceutically acceptable carriers or excipients.

* * * * *